United States Patent [19]

Shockley, Jr. et al.

[11] Patent Number: 5,641,458

[45] Date of Patent: Jun. 24, 1997

[54] FLOW THROUGH CELL ASSEMBLY

[76] Inventors: H. David Shockley, Jr., 1510 Hartford, Austin, Tex. 78703; William R. Wilkinson, 8033 Sunset Blvd. #684, Los Angeles, Calif. 90046

[21] Appl. No.: 490,683

[22] Filed: Jun. 15, 1995

[51] Int. Cl.$^6$ .................................................. G01N 21/05
[52] U.S. Cl. .................... 422/102; 422/103; 422/55; 436/68
[58] Field of Search .................. 422/101, 68, 48, 422/81, 86, 55, 104, 103; 436/68, 172

[56] References Cited

U.S. PATENT DOCUMENTS

| | | | |
|---|---|---|---|
| 2,913,386 | 11/1959 | Clark, Jr. | 204/195 |
| 3,413,095 | 11/1968 | Bramson | 23/258.5 |
| 3,595,079 | 7/1971 | Grahn | 73/204 |
| 3,627,137 | 12/1971 | Bier | 210/321 |
| 3,630,207 | 12/1971 | Kahn et al. | 128/350 R |
| 3,649,199 | 3/1972 | Littlejohn | 23/230 B |
| 3,684,097 | 8/1972 | Mathewson et al. | 210/321 |
| 3,757,947 | 9/1973 | Wakefield et al. | 210/86 |
| 3,763,422 | 10/1973 | MacPhee et al. | 324/30 R |
| 3,826,730 | 7/1974 | Watanabe et al. | 204/195 P |
| 3,834,544 | 9/1974 | Tyson, Jr. et al. | 210/321 |
| 3,907,687 | 9/1975 | Hoeltzenbein | 210/321 |
| 3,932,283 | 1/1976 | Esmond | 210/321 |
| 3,977,976 | 8/1976 | Spaan et al. | 210/321 |
| 3,980,564 | 9/1976 | Bardin et al. | 210/321 |
| 3,998,717 | 12/1976 | Watson et al. | 204/195 P |
| 4,003,707 | 1/1977 | Lübbers et al. | 23/232 |
| 4,021,933 | 5/1977 | Hughes | 35/10 |
| 4,038,191 | 7/1977 | Davis et al. | 210/321 |
| 4,041,932 | 8/1977 | Fostick | 128/26 |
| 4,168,293 | 9/1979 | Bramson | 422/46 |
| 4,181,245 | 1/1980 | Garrett et al. | 222/450 |
| 4,184,962 | 1/1980 | Oscarsson et al. | 210/232 |
| 4,208,902 | 6/1980 | Kim et al. | 73/19 |
| 4,272,484 | 6/1981 | Lubbers | 422/68 |
| 4,272,485 | 6/1981 | Lubbers | 422/68 |

(List continued on next page.)

FOREIGN PATENT DOCUMENTS

| | | |
|---|---|---|
| 726863 | 2/1966 | Canada . |
| 013611 | 7/1980 | European Pat. Off. . |
| 065402 | 11/1982 | European Pat. Off. . |
| 56-747 | 4/1982 | Japan . |
| 979117 | 1/1965 | United Kingdom . |
| 1346533 | 2/1974 | United Kingdom . |
| 2059070 | 4/1981 | United Kingdom . |
| 2095409 | 9/1982 | United Kingdom . |
| PCT 80/02794 | 12/1980 | WIPO . |

OTHER PUBLICATIONS

Klein, et al.; Report of Study Group for the Artificial Kidney–Chronic Uremia Program; 1977; U.S. Dept. of Health, Education and Welfare, U.S. Pub. No. (NIH) 77–1294; Bethesda Maryland.

M. Gutcho; Artificial Kidney Systems; 1970; pp. 1–318.

Babb, et al; Methods for the In Vivo Determination of Membrane Permeabilities and Solute Diffusivities; 1968; vol. XIV Trans. Amer. Soc. Artif., pp. 25–30.

Kent Tech. Rev., An Automatic Dissolved Oxygen System; No. 15, pp. 17–19; Feb., 1976.

Berman; Gas Sensors based on the Metaliased Membrane Electrode; Nov. 1974; Conference on Environmental Sensors and Applications, London, Eng., pp. 67–80.

*The Acid–Base Status of the Blood,* by Ole Siggaard–Andersen, 4th edition, 1974, pp. 171–173.

*Primary Examiner*—Lyle A. Alexander
*Attorney, Agent, or Firm*—Matthews & Associates, L.L.P.

[57] ABSTRACT

A flow through cell for non-invasive monitoring of fluids flowing therethrough includes a membrane covered view window through which sensors may monitor the fluids. The membranes are secured in position by a frame and retainer assembly with the frame and retainer clamping the membranes in place between the frame support structure and the retainer. The frame is snugly fitted into the cell and includes a sensor receptive chamber for positioning the sensors in the window and in position with the membranes.

5 Claims, 3 Drawing Sheets

U.S. PATENT DOCUMENTS

| | | | |
|---|---|---|---|
| 4,306,877 | 12/1981 | Lubbers | 23/230 R |
| 4,308,230 | 12/1981 | Bramson | 422/48 |
| 4,309,592 | 1/1982 | Le Boeuf | 219/299 |
| 4,310,416 | 1/1982 | Tanaka et al. | 210/321.3 |
| 4,323,455 | 4/1982 | Tanaka et al. | 210/321.2 |
| 4,332,264 | 6/1982 | Gortz et al. | 134/57 R |
| 4,338,174 | 7/1982 | Tamura | 204/195 P |
| 4,370,983 | 2/1983 | Lichtenstein | 128/630 |
| 4,400,242 | 8/1983 | Albery et al. | 204/1 T |
| 4,404,100 | 9/1983 | Mikhail | 210/232 |
| 4,405,197 | 9/1983 | Bejczy | 350/96.15 |
| 4,410,020 | 10/1983 | Lorenz | 141/65 |
| 4,411,872 | 10/1983 | Bramson | 422/310 |
| 4,415,447 | 11/1983 | Foucras et al. | 210/321.1 |
| 4,529,495 | 7/1985 | Marsoner | 204/411 |
| 4,557,900 | 12/1985 | Heitzmann | 422/55 |
| 4,640,820 | 2/1987 | Cooper | 422/68 |
| 4,786,474 | 11/1988 | Cooper | 422/68 |
| 4,798,738 | 1/1989 | Yafuso et al. | 427/2 |
| 4,824,789 | 4/1989 | Yafuso et al. | 436/68 |
| 5,289,255 | 2/1994 | Mullin et al. | 356/246 |

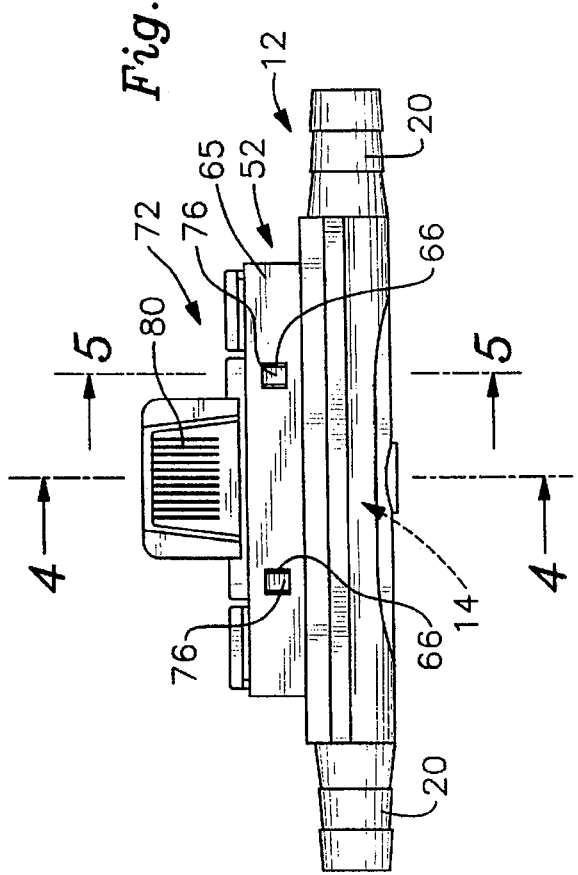
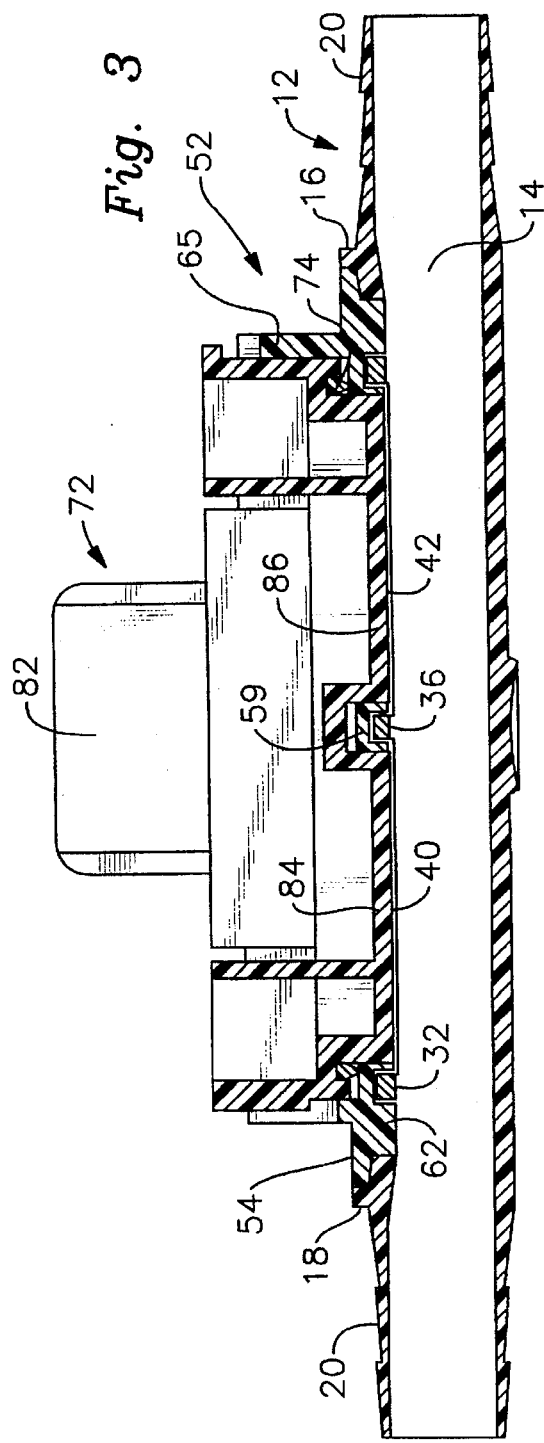

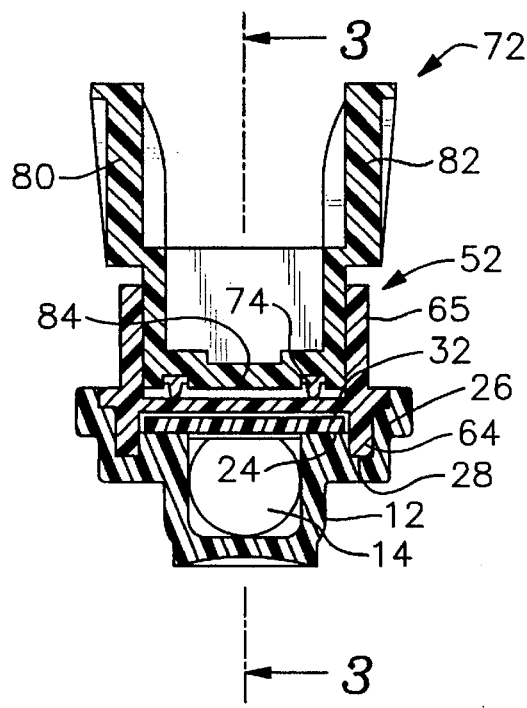
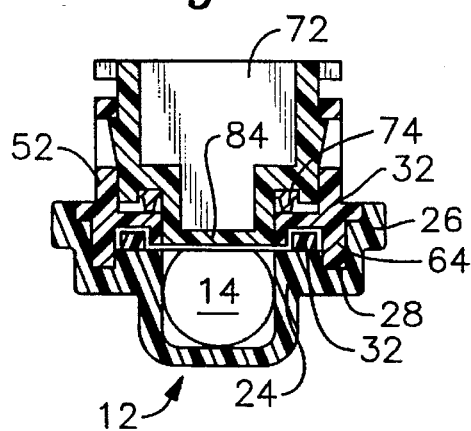
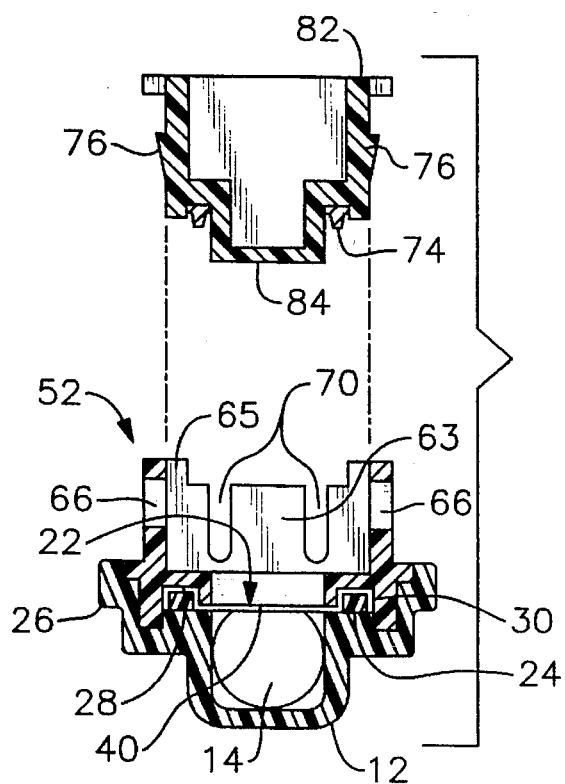

FLOW THROUGH CELL ASSEMBLY

BACKGROUND OF THE INVENTION

1. Field of the Invention

The subject invention is generally related to a cell which is inserted in the fluid flow line in such a manner to permit non-invasive monitoring of the fluid and is specifically directed to an assembly permitting sensors to interface with the fluid through semi-permeable membranes thereby allowing for photochemical reaction which may in turn be optically monitored through windows provided in the sensors. This combination provides for non-invasive real time monitoring of various entities contained in the fluid.

2. Description of the Prior Art

In most medical applications where fluids are either being introduced into the body or withdrawn from the body, the purity of the fluid must be maintained. Where such fluids have to be pumped, monitored, or subjected to temperature and other environmental controls, these activities must be done in a non-invasive manner. Over the years, a widely used non-invasive monitoring technique has been developed where the fluid is exposed to a light emitting device and a sensor, wherein the reflected light spectrum as modified by the photochemical reactions between the sensor elements and certain specific constituents within the fluid is monitored to determine the presence or lack of specific constituents, as well as the concentration of the constituents. The practice has become a widely accepted method for monitoring and diagnosing the condition of human blood. This methodology is particularly useful during the conduct of Cardio Pulmonary Bypass during open heart surgery because the information is received by the technician immediately.

A well known device specifically directed to directing a flow of blood through a photochemical monitoring zone is the Cardiovascular Devices Inc. (CDI) flow through cell, models 6640, 6630 and 6620, generally shown and described in U.S. Pat. Nos. 4,460,820 and 4,786,474. As there shown, the cell includes a flow through body having a window opening covered by a membrane. Sensors are seated adjacent to the membrane and may monitor the blood passing through the cell. While this device has gained widespread commercial acceptance over the last decade, there are several drawbacks which make it cost prohibitive in certain applications and certainly increase the costs of treatment wherever it is used as part of the diagnostic regimen. This is particularly true since such units are disposable and costs associated with their use is repeated each time the technique is employed.

One of the problems driving up the cost of the CDI cell is the assembly design coupled with the labor intensive methods required for fabrication. As particularly described in U.S. Pat. No. 4,640,820, the flow through cell includes a membrane support and a pair of membranes for isolating the sensors from the flowing blood. The means for mounting the membranes in the window under the lens of the sensor includes a groove in the support structure for receiving the edge portions of the membrane. Typically, two different membranes are utilized, each having a different optical response and a different permeability factor, depending on the application. In order to mount the membranes in the window, the edge portion of the first membrane is extended into the groove in the structure separating the two windows and the second membrane is extended over the retaining means outwardly from the groove and then into the groove in order to form a smooth transition with the first membrane. Specifically, one of the membranes is wrapped partially around the retainer which is then inserted in the groove.

As described in the '820 patent, a region of the end portion of one membrane extends beyond the end portion of the second membrane within the groove and is adhered to the wall of the groove. This allows a portion of the first membrane to be adhered directly to the support even if only one face of the membrane is capable of being adhesively attached. It is this wrapping feature which establishes the proper firmness of the membranes in the assembly.

While effective for the purpose of joining the adjacent edges of the two membranes, the remaining three sides of each of the two membranes must also be sealed in a separate groove around the perimeter of the cell and the quality of this seal is impaired by the excess material resulting from the aforementioned wrapping technique. The complicated wrapping technique and placement steps as defined in the '820 patent has resulted in an increase in costs while at the same time reducing the reliability of the assembly due to both the skill required and the narrow tolerances which must be maintained to assure a proper fit of the membranes in the cell.

Therefore, there remains a need for a high quality, low cost cell capable of being used in the existing equipment as a disposable flow through cell for non-invasive monitoring of bodily fluids, especially blood.

SUMMARY OF THE INVENTION

The subject invention is specifically directed to an improved flow through cell which maintains the high quality and high reliability standards of the prior art cells while being constructed with much less complexity and at a lower cost. In the preferred embodiment, the flow through cell of the subject invention includes a flow through body having nipple type connectors at opposite ends whereby the body may be inserted, in-line, in a fluid flow line as is customary for such devices. The upper side of the body is open to provide a window through which photochemical sensors and photo-optical transducers may monitor the fluid flowing therethrough a pair of stepped recess seats are provided about the perimeter of the window opening to accommodate the frame-membrane assembly. The geometry of the frame provides bonding surfaces which easily mate with the aforementioned recess seats and bond reliably with normal adhesives using easily learned skills.

The frame generally defines a pair of window openings which accommodate two membranes. A groove surrounds the perimeter of the two windows in the frame structure and the two windows share the groove between them such that the groove generally defines a squared off figure eight and provides a groove on all four sides of each membrane window. A pair of membranes are loosely placed over the windows and automatically aligned by the step geometry of the frame used in the assembly of the frame to the body. A retaining member which is generally shaped so as to fill the figure eight groove around the two windows, is pressed into the groove thereby trapping all four edges of both membranes simultaneously between the retainer inner and outer wall surfaces and the frame groove inner and outer wall surfaces. An adhesive may be used to supplement this mechanical assembly prior to final assembly to the body member.

The frame also serves as the receiver for the sensors and permits the sensors to be placed in close proximity to the membranes. In the preferred embodiment, a removable cover is placed in the frame so as to guard against contamination, damage to the membranes and leakage prior to insertion of the sensor.

Typically, the membrane and frame are secured in the cell by adhesive means, sonic welding or the like. The retainer and membranes are likewise secured in the assembly.

The flow through cell structure of the present invention permits the membranes to be assembled flat on the frame and cell body, and to be secured in place with a retainer "clamp". This greatly reduces the labor required in assembly, it relieves the tolerances required for a secure membrane assembly, and it reduces the skill level required for assembly when compared to the prior art devices. The clamping provided by the retainer assures proper tautness of the membranes in the window opening, assuring consistent and proper responsiveness of the sensor.

It is, therefore, an objective and feature of the subject invention to provide an improved flow through cell for non-invasive monitoring of fluids flowing therethrough.

It is a further objective and feature of the subject invention to provide a flow through assembly which is of high reliability while at the same time is simple to manufacture and assemble.

It is an additional objective and feature of the subject invention to provide a flow through cell maintaining the high performance standards of prior art cells while at the same time permitting a reduction in cost through the relief of tolerance requirements, reduction of labor cost and improvement in reliability and yield of assemblies produced.

Other objectives and features will be readily apparent from the accompanying drawings and description of the preferred embodiment.

BRIEF DESCRIPTION OF THE DRAWINGS

FIG. 2 is a side plan view of the assembled flow through cell of FIG. 1.

FIG. 3 is a longitudinal cross-sectional of the flow through cell as shown in FIG. 2, and taken along the lines 3—3 of FIG. 4.

FIG. 4 is a lateral cross-sectional view of the flow through cell taken along lines 4—4 of FIG. 2.

FIG. 5 is a lateral cross-sectional view of the flow through cell taken along lines 5—5 of FIG. 2.

FIG. 6 is a lateral cross-sectional view of the flow through cell taken along lines 5.5 of FIG. 2 and similar to FIG. 5, but showing the cover removed.

DETAILED DESCRIPTION OF THE PREFERRED EMBODIMENT

Figure 1:
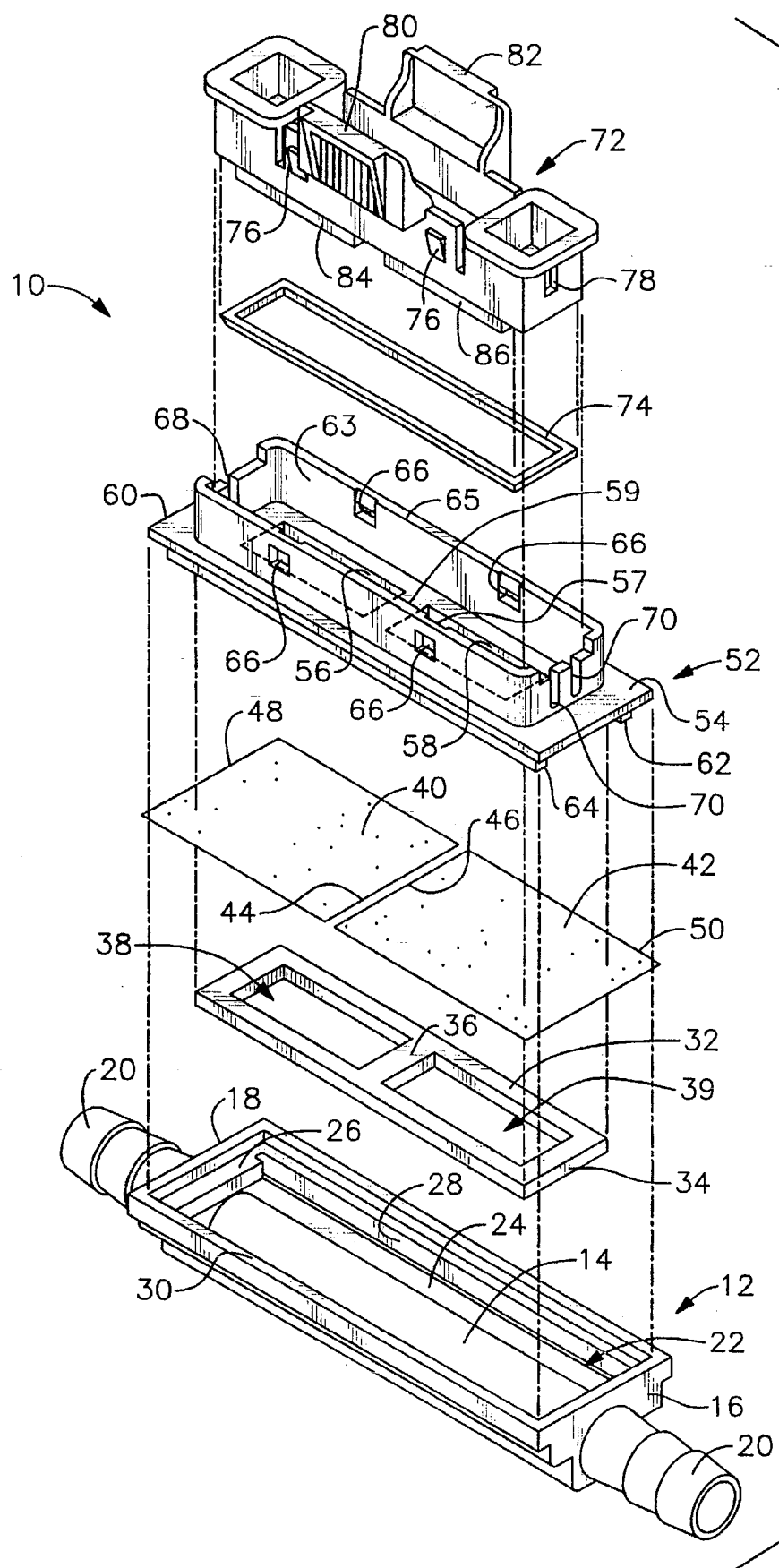
FIG. 1 is an exploded perspective view of the flow through cell assembly of the preferred embodiment.

The components of the flow through cell 10 of the preferred embodiment are shown in exploded, pre-assembled form in FIG. 1.

The cell body 12 includes an axial, through chamber 14. The end walls 16 and 18 of the body include openings in communication with the chamber 14 and having integral connectors, such as, by way of example, the ribbed nipple connectors 20, by which the cell may be coupled, in-line, in a fluid flow line.

The upper side of the body 12 is open, providing a window 22. As best shown in FIGS. 1 and 4–6, the perimeter of the window 22 is defined by a first recessed seat of ledge 24. Outboard of ledge 24 is a stepped or raised second recessed seat 26. Between the seats 24 and 26 is a longitudinal groove or channel 28 running down both sides of the body 12. A raised outer wall 30 defines the upper peripheral edge of the cell body 12.

A retainer 32 is adapted to allow it to fit against the first seat 24, inwardly of the channel 28, as best shown in FIGS. 3–6. The retainer 32 is substantially flat and includes outer perimeter walls 34 and a crossmember 36 for defining two sensor windows 38 and 39, which are aligned with cell body window 22, when assembled.

Typically, a separate membrane 42 and 40 is associated with each window 38 and 39, respectively, although a single membrane could be used. The inner edge 44 of membrane 42 and the inner edge 46 of membrane 40 are in an overlapping relationship and each are located over crossmember 36 of the retainer 32. The remaining outer edge portion 48 and 50 of the respective membranes extend beyond the outer perimeter walls 34 of the retainer 32.

A frame 52, as best shown in FIG. 1, has a substantially rectangular base 54 with interior openings or windows 56 and 58 which correspond with the windows 38 and 39, respectively, of the retainer 32. As best shown in FIGS. 3–6, the outer perimeter edge 60 of the frame base 54 fits snugly in the recessed seat 26. The frame has a pair of longitudinal, downwardly extending runners 62 and 64, adapted to be received in the channel 28 of the cell body. The frame 52 is positioned against the retainer 32 and the membranes 40 and 42 such that the outer edges 44, 46, 48 and 50 are trapped in a mating groove to the retainer 32 in the frame 52 causing the edges 44, 46, 48 and 50 of membranes 40 and 42 to fold around the walls 34 and cross member 36 of the retainer 32, thereby clamping the membranes in place with the desired firmness. Typically, adhesive may be applied to the contact surfaces of the retainer 32 and the frame 52 to secure the assembly. In the preferred embodiment, the frame 52 includes a frame crossmember 59 positioned in alignment with the crossmember of the retainer to engage the overlapping edges 44 and 46 of the two membranes 40 and 42, respectively.

An upper, sensor receptive chamber 63 is provided in the frame 52 and is defined by the upstanding wall 65. The various slots and openings in the wall 65 are adapted to mate with the specific sensors being utilized and are not an important feature of the invention. However, openings 66 are typically designed to receive detent retainers for holding the flow through cell in the appropriate position on the sensor body, and the slots 68 and 70 provide for proper alignment.

A cover assembly 72 is provided for protecting the exposed membranes 40 and 42 against damage during storage and shipment for supporting the membranes against internal fluid pressures that might exist prior to inserting the sensors, for guarding against fluid leaks which might occur through the semi-permeable membranes prior to inserting the sensors and for protecting the membrane surface from contamination during shipment, storage or use prior to inserting the sensor. In the preferred embodiment, a resilient seal 74 is positioned on the perimeter of the cover assembly 72 to seal between the chamber wall 65 and the membrane window openings 56 and 58 of the frame 52. The cover includes a plurality of detent tabs 76 adapted to be received in the receptive openings 66 of the frame wall 65 for securing the cover in place. Alignment tabs 78 may also be provided to mate with slots 68, 70, where desired. Upstanding thumb and finger tabs 80 and 82 are provided whereby the cover may be grasped and slightly squeezed so as to release the detent tabs 76 for removing the cover from the assembly. In the preferred embodiment, and as best shown in FIGS. 3, 5 and 6, the cover includes lower abutment surfaces 84 and 86, which engage the respective membranes and maintain them in a flat condition during shipment, storage and internal pressurization without a sensor present.

The assembled cell comprises the body 12, the retainer 32, the membranes 40 and 42, and the frame 52. The removable cover comprises the cover assembly 72 and the seal 74. When in use, the cover and seal are removed and the sensors are inserted in place of the cover in the sensor chamber or receptacle 63 of the frame of the assembled cell and positioned relative to the respective membranes 40 and 42 in alignment with the respective frame windows 56 and 58.

From the foregoing, it will be readily understood that the invention provides an improved, reliable, high quality flow through cell assembly. While certain features and embodiments of the invention have been described in detail herein, it will be apparent the invention includes all modifications and enhancements within the scope and spirit of the following claims.

What is claimed is:

1. A flow through cell assembly consisting essentially of:

a cell body defining an internal chamber, said body having at least one opening in communication with said internal chamber for monitoring fluids therein, and an inlet and an outlet for connecting said cell body in an in-line flow system;

a retainer having an outer wall defining a monitoring window, said retainer positioned within said opening of said cell body;

a membrane positioned on top of said retainer; and a clamping frame mounted over said retainer peripherally clamping said membrane over said retainer outer wall tensioning said membrane when assembled.

2. The flow through cell assembly of claim 1, wherein: said clamping frame defines a receptive chamber for receiving a sensor for monitoring said fluid within said internal chamber of said cell body.

3. The flow through cell assembly of claim 2, further including:

a removable cover placeable in said receptive chamber.

4. The flow through cell assembly of claim 3, wherein: said removable cover includes a resilient seal.

5. A flow through cell assembly consisting essentially of:

a cell body defining an internal chamber, said body having at least one opening in communication with said internal chamber for monitoring fluids therein, and an inlet and an outlet for connecting said cell body in an in-line flow system;

a retainer having an outer wall defining a monitoring window, said retainer positioned within said opening of said cell body;

a membrane positioned on top of said retainer;

a clamping frame mounted over said retainer peripherally clamping said membrane over said retainer outer wall tensioning said membrane when assembled;

a receptive chamber formed by said clamping frame for receiving a sensor for monitoring said fluid within said internal chamber of said cell body; and a removable cover placeable in said receptive chamber for sealably covering said membrane.

* * * * *